US009750907B2

(12) United States Patent
Librett et al.

(10) Patent No.: US 9,750,907 B2
(45) Date of Patent: *Sep. 5, 2017

(54) PORTABLE POSITIVE AIRWAY PRESSURE APPARATUS AND METHOD FOR ATTENUATING THE NOISE EMITTED THEREFROM

(71) Applicant: Human Design Medical, LLC, Newton, MA (US)

(72) Inventors: Kevin Scott Librett, Watertown, MA (US); Karl R Leinsing, Dover, NH (US)

(73) Assignee: Human Design Medical, LLC, Newton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/216,922

(22) Filed: Mar. 17, 2014

(65) Prior Publication Data

US 2014/0299130 A1    Oct. 9, 2014

Related U.S. Application Data

(60) Provisional application No. 61/798,367, filed on Mar. 15, 2013, provisional application No. 61/798,541, filed on Mar. 15, 2013.

(51) Int. Cl.
*F04D 29/66*     (2006.01)
*A61M 16/00*   (2006.01)
(Continued)

(52) U.S. Cl.
CPC .... *A61M 16/0066* (2013.01); *A61M 16/0051* (2013.01); *A61M 16/0069* (2014.02); *A61M 16/06* (2013.01); *A61M 16/0816* (2013.01); *A61M 16/0858* (2014.02); *A61M 16/0875* (2013.01); *A61M 16/107* (2014.02); *F04D 29/4213* (2013.01); *F04D 29/4226* (2013.01); *F04D 29/663* (2013.01); *F04D 29/664* (2013.01); *F04D 29/665* (2013.01); *G10K 11/04* (2013.01); *G10K 11/161* (2013.01);
(Continued)

(58) Field of Classification Search
CPC ............ A16M 16/0066; F04D 29/4213; F04D 29/4226; F04D 29/663; F04D 29/665; F04D 29/664; F06D 2250/51; F06D 2260/963
See application file for complete search history.

(56) References Cited

U.S. PATENT DOCUMENTS 7,112,038 B2* 9/2006 Curtis .................. F04D 29/665
                                                        181/225
7,789,194 B2* 9/2010 Lathrop ............ A61M 16/0066
                                                        181/212
(Continued)

*Primary Examiner* — Ninh H Nguyen
(74) *Attorney, Agent, or Firm* — Ascentage Patent Law, LLC; Travis Lee Johnson; David S. Einfeldt

(57) ABSTRACT

The systems and methods described herein provide a quiet, light-weight, and portable system and apparatus for providing positive air pressure to a patient. The systems may include a housing with an inlet port, a vibrationally isolated blower unit positioned in an inner chamber, and an outlet port for delivery of the pressurized air from the blower unit. The inlet port and outlet port may each have a tube with dimensions that are defined in relation to the inner chamber so as to reduce the overall noise output of the system.

16 Claims, 8 Drawing Sheets

(51) Int. Cl.
*F04D 29/42* (2006.01)
*A61M 16/08* (2006.01)
*G10K 11/04* (2006.01)
*G10K 11/16* (2006.01)
*A61M 16/10* (2006.01)
*A61M 16/06* (2006.01)

(52) U.S. Cl.
CPC . *A61M 16/0063* (2014.02); *A61M 2016/0027* (2013.01); *A61M 2205/3355* (2013.01); *A61M 2205/42* (2013.01); *A61M 2205/50* (2013.01); *A61M 2205/502* (2013.01); *A61M 2205/505* (2013.01); *A61M 2205/75* (2013.01); *A61M 2205/8206* (2013.01); *A61M 2207/00* (2013.01); *F05D 2250/51* (2013.01); *F05D 2260/96* (2013.01); *Y10T 29/49826* (2015.01)

(56) References Cited

U.S. PATENT DOCUMENTS

| | | | | |
|---|---|---|---|---|
| 8,006,691 B2* | 8/2011 | Kenyon | ............ | A61M 16/0051 122/4 R |
| 8,375,944 B2* | 2/2013 | Kwok | .................. | A61M 16/06 128/204.18 |
| 8,931,481 B2* | 1/2015 | Jones | ................ | A61M 16/0066 128/204.18 |
| 9,132,252 B2* | 9/2015 | Barlow | ............ | A61M 16/0066 |

\* cited by examiner

PORTABLE POSITIVE AIRWAY PRESSURE APPARATUS AND METHOD FOR ATTENUATING THE NOISE EMITTED THEREFROM

CROSS-REFERENCE TO RELATED APPLICATIONS

This application claims the benefit of U.S. Patent Application 61/798,367 filed on Mar. 15, 2013 and U.S. Patent Application 61/798,541 filed on Mar. 15, 2013 which are incorporated herein by reference.

COPYRIGHT STATEMENT

A portion of the disclosure of this patent application document contains material that is subject to copyright protection including the drawings. The copyright owner has no objection to the facsimile reproduction by anyone of the patent document or the patent disclosure as it appears in the Patent and Trademark Office file or records, but otherwise reserves all copyright rights whatsoever.

BACKGROUND OF THE INVENTION

1. Field of the Invention

The present invention relates to medical devices, and, more particularly to devices providing positive airway pressure [PAP] such as continuous positive airway pressure [CPAP] devices, automatic positive airway pressure devices [APAP], variable positive airway pressure devices [VPAP], and bi-level positive airway pressure devices [BPAP].

2. Description of the Prior Art

It is known that applying a CPAP device to a patient may prevent upper airway occlusion during sleep. CPAP devices have become the apparatus of choice for the treatment of chronic sleep apnea, chronic pulmonary obstruction and snoring. Many CPAP machines are readily available in the marketplace.

A typical CPAP system generally includes a bedside generator comprising, a blower unit powered by an electric motor. The blower unit, the motor, and associated controls are usually encased together within the bedside generator. A delivery tube, usually a flexible plastic tube having a proximal end and a distal end, is used to deliver pressurized air or other gasses to the patient. The proximal end of the delivery tube is connected to the bedside generator and the distal end of the delivery tube is fitted to the face of a patient. The patient interface may include features that allow the patient interface to be affixed to the patient and maintain a proper orientation with respect to the patient.

Bedside CPAP machines are typically large and heavy. They are usually plugged into a wall outlet for power or have a large external battery. The size, weight, and power constraints can interfere with patients' ability and willingness to use the machine. For example, these constraints can make it difficult to utilize the CPAP apparatus in areas away from their bedside or while traveling. Additionally, these constraints can also prohibit patients from moving freely during sleep, thereby inducing further discomfort.

Furthermore, typical CPAP devices are relatively loud and can interfere with a patient's sleep or the sleep of other people nearby. In a typical CPAP device, sound may be propagated from various locations and actions of the device, such as the flow of air the flow of air into and out of the device or the operation of the motor and fan. Because the apparatus is used mainly in a bedroom or other place having a low ambient noise level to facilitate sleep, it is important that the blower operates quietly so as not to disturb the patient or others in close proximity while they sleep.

A need therefore exists for PAP devices with size, weight, and sound characteristics that provide improved usability for patients.

SUMMARY OF THE INVENTION

The system and methods described herein provide a CPAP apparatus that can be held and operated in one hand, is portable, and is quieter than 30 decibels, quieter than 28 decibels (dBA) while in operation, quieter than 27 dBA and in some cases quieter than 26 dBA.

In an exemplary embodiment, the current application discloses an CPAP apparatus comprising: dual sealed chambers connected in series, each having an inlet port that is proportional in size to its respective chamber; a motor or blower that is placed within the second chamber, wherein vibrations from the motor or blower are isolated or substantially isolated from the second chamber and/or housing; and in some embodiments a foam or other noise attenuating material may be added to further attenuate the amount of noise heard by the patient. In some embodiments noise attenuating units comprised of angled plates, circuitous paths and other acoustically obstructive and positioned units are strategically placed inside the acoustic chambers near the inlets.

In at least one embodiment, aside from the inlet port and the blower outlet port, the CPAP apparatus is otherwise hermetically sealed. In additional embodiments, the blower outlet port may extend or connect to a patient interface system, which may include a tube or mask.

A method for reducing the amount of noise released from a portable CPAP device while in operation, comprising the steps of providing a housing wherein the housing defines a first and a second acoustic chamber, routing the flow of air through a first inlet port that is sealed from and passes through the second acoustic chamber into the first acoustic chamber; routing the flow of air from the first acoustic chamber into the second acoustic through a second inlet port, wherein a blower is mounted within the second acoustic chamber; and routing the flow of air from the second acoustic chamber through and outlet port that is sealed from and passes through the first chamber.

The method may further comprise the step of balancing an acoustic low pass filter design based on the proportionality of a length and cross-sectional area of the first inlet port with the volume of the first acoustic chamber against any increase in noise generated by the blower positioned in the second acoustic chamber caused by additional work required to maintain a desired amount of air flow.

Single acoustic chamber embodiments are also disclosed herein wherein the majority of the length of the inlet port into the acoustic chamber is disposed within the chamber and the length and cross-sectional area of the inlet port are defined by the volume and length of the acoustic chamber, such that a low pass acoustic filter is created to balance against any increase in noise caused by additional work performed by a blower disposed inside the acoustic chamber.

In all of the embodiments the blower may also be vibrationally isolated from the chamber in which it is disposed.

These and other embodiments are described in more detail herein.

BRIEF DESCRIPTION OF THE DRAWINGS

The foregoing and other objects, aspects, features, and advantages of the disclosure will become more apparent and better understood by referring to the following description taken in conjunction with the accompanying drawings, in which.

DETAILED DESCRIPTION OF THE PREFERRED EMBODIMENT

To provide an overall understanding of the systems, devices, and methods described herein, certain illustrative embodiments will be described. Although the embodiments and features described herein are frequently described for use in connection with CPAP apparatuses, systems, and methods, it will be understood that all the components, mechanisms, systems, methods, and other features outlined below may be combined with one another in any suitable manner and may be adapted and applied to other PAP apparatuses, systems, and methods, including, but not limited to, automatic positive airway pressure devices [APAP], variable positive airway pressure devices [VPAP], bi-level positive airway pressure devices [BPAP], and related apparatuses, systems, and methods.

Bedside CPAP machines are typically large, heavy, and noisy. The systems and methods described herein are directed towards a small, quiet, light-weight, and portable CPAP device to overcome this current limitations and disadvantages. A typical CPAP device on the market weighs at least 16 ounces or more. The system and methods described herein may be used to provide a PAP device, such as a CPAP device, weighing 10 ounces or less.

Figure 1:
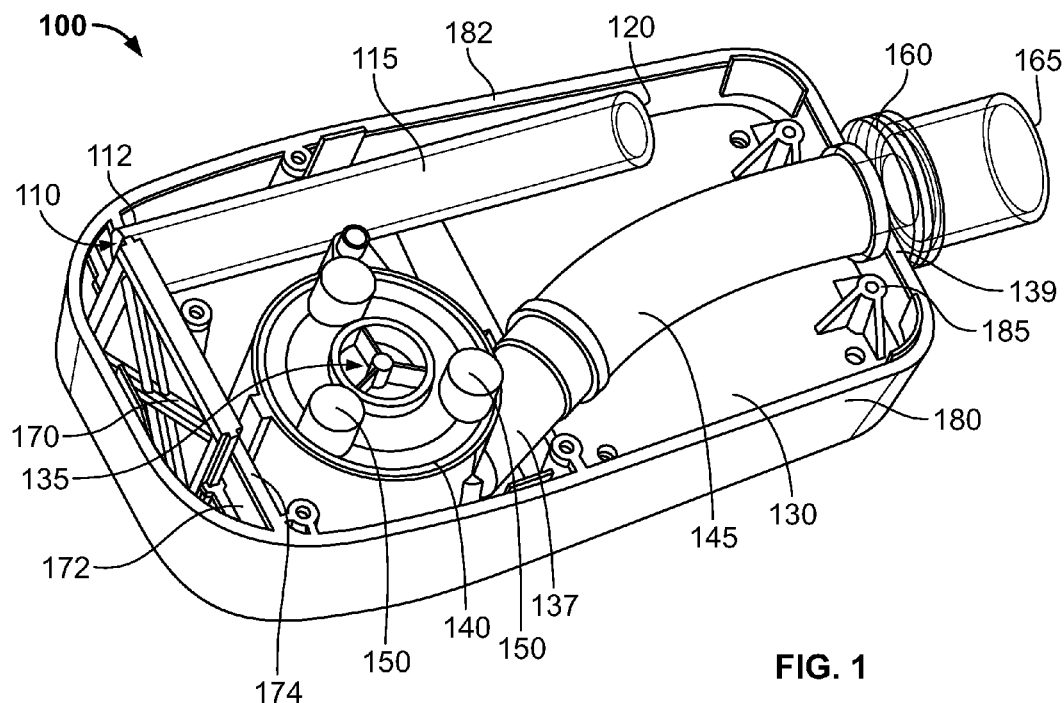
FIG. 1 is a perspective view of the interior of a PAP apparatus.

FIG. 1 depicts the interior of a PAP apparatus, such as a CPAP device. CPAP device 100 has a lower housing component 180, which together with an upper housing component (not shown) defines a sealed chamber 130. Sealed chamber 130 has an inlet port 110 and an outlet port 139. A motor or blower 140 is placed within chamber 130. In certain approaches, device 100 includes a pre-intake chamber 172. Pre-intake chamber 172 may be separated from sealed chamber 130 by wall 174. Pre-intake chamber 172 serves to prevent the occlusion of inlet port 110 during use of device 100, and may also include filter 170.

In some embodiments, foam or another anechoic material may be placed within chamber 130 to further attenuate noise produced during the operation of device 100. The anechoic or noise attenuating material may be secured at specific locations within each chamber, such as along the housing (e.g., housing 180), tubes (e.g., tube 115 and 145), and blower (e.g., blower 140). In certain embodiments, the lower and/or upper housing components may be lined with an anechoic or noise attenuating material. In such embodiments, the anechoic or noise attenuating material may include foam, rubber, clay, silicon, or any other suitable soft and/or porous materials.

In certain approaches, blower 140 is secured to chamber 130 using one or more mount connects 150. In some embodiments, mount connect 150 may further comprise pivoting cone connectors, circular donut shaped mount connects, a silicone cradle, or any combination thereof. For example, mount connect 150 may comprise pivoting cone connectors that connect the top of blower 140 within chamber 130 and circular donut shaped mount connects that connect the bottom of blower 140 within chamber 130. In addition to connecting blower 140 to the housing, mount connects 150 may reduce or eliminate transfer of vibrations from blower 140 to other components of device 100. In certain embodiments, blower 140 is a brushless air-bearing motor.

Device 100 additionally includes connector portion 185 to couple lower housing 180 and upper housing together, thereby creating a seal. In the depicted example, connector portions 185 are around the perimeter of the housing. A fastener, such as a screw, may be used to couple the housing. Additionally or alternatively, edge 182 of the housing may provide a coupling and/or sealing mechanism. For example, edge 182 may have a tongue and groove. Edge 182 may also include a seal, such as santoprene or silicone.

In certain embodiments, inlet port 110 includes an intake tube 115 having a first end 112 through wall 174 and a second end 120 that extends into chamber 130. Intake tube 115 may have either a constant or varying internal diameter ranging from approximately 0.25 inches to approximately 0.75 inches and may have a length ranging from approximately 0.25 inches to approximately 3 inches, although any appropriate diameter and length may be used. The length and diameter of intake tube 115 affect the overall noise attenuation of the CPAP device, as will be further discussed below, for example, in relation to FIG. 2, equation 1, and equation 2. Accordingly, in some approaches, the dimensions of intake tube 115 are proportionally related to the volume of chamber 130.

Intake tube 115 may be formed using rigid materials, flexible materials, or any combination thereof. For example, intake tube 115 may be formed using a hard plastic. In certain embodiments, intake tube 115 is composed of flexible polyvinylchloride (PVC) tubing, silicone tubing, or any other type of tubing commonly used in the art.

In certain approaches, outlet port 139 includes outlet tube 145, which extends from blower outlet 137 through the housing. An adapter 160 may be used to connect blower outlet tube 145 to patient interface 165. Adapter 160 may be solitary in construction and configured so that a proximal portion of adapter 160 may be secured and sealed to the housing of device 100, while a distal portion of adapter 160 extends outward from device 100. Additionally or alternatively, adapter 160 may be removably coupled to the housing components. Lower housing component 180 and the upper housing component may each include a detent (not pictured) capable of accepting a portion of the adapter, whereby the two housing components together form a seal around the circumference of a portion of the adapter.

Outlet tube 145 may also vary in length and diameter. The length of blower outlet tube 145 is long enough to connect to outlet 137 of blower 140 through outlet port 139. Outlet tube 145 provides a sealed airway between blower 140 and adapter 160 and/or patient interface system 165. Additionally, depending on the dimensions of the blower 140, the inner diameter of the outlet tube 145 may vary so long as the diameter is large enough to fit over and seal with outlet 137, and adapter 160 or patient interface system 165. Outlet tube 145 may be formed using rigid materials, flexible materials, or any combination thereof. For example, outlet tube 145 may be formed using a hard plastic. In certain embodiments, outlet tube 145 is composed of flexible polyvinylchloride (PVC) tubing, silicone tubing, or any other type of tubing commonly used in the art.

In certain embodiments, pre-intake chamber 172 includes a filter 170 to clean the air of particulate matter. In certain embodiments, pre-intake chamber 172 is removable from sealed chamber 130 and other components of device 100 so that it may be cleaned, replaced, or adapted for a particular need. For example, various types of filters may be used for filter 170 depending on a patient's health. Filter 170 may not be required for all patients, may be replaceable, or may be cleaned.

During operation, PAP device 100 creates positive air pressure through outlet port 139. For example, when patient interface 165 is attached, PAP device 100 creates positive air pressure, which can be provided to the patient when the patient places patient interface 165 at his or her airways (e.g., nose or mouth). Blower 140 includes intake 135. When blower 140 is powered on, blower 140 intakes air through intake 135 and pushes out that air through outlet 137. The reduced pressure at intake 135 causes air to flow through inlet port 110 into chamber 130, where it then flows into intake 135 of blower 140, and is pushed by blower 140 through outlet 137, through outlet tube 145, and through outlet port 139 to thereby provide positive air pressure through outlet port 139. In certain embodiments, air may be passed through pre-intake chamber 172, before entering inlet port 110. In certain approaches, the pressurized air is delivered to a patient through patient interface 165 at a pressure ranging from approximately 2 centimeters (cm) of water to approximately 40 cm of water above atmospheric pressure at the point of use, although any appropriate pressure may be used.

Figure 2:
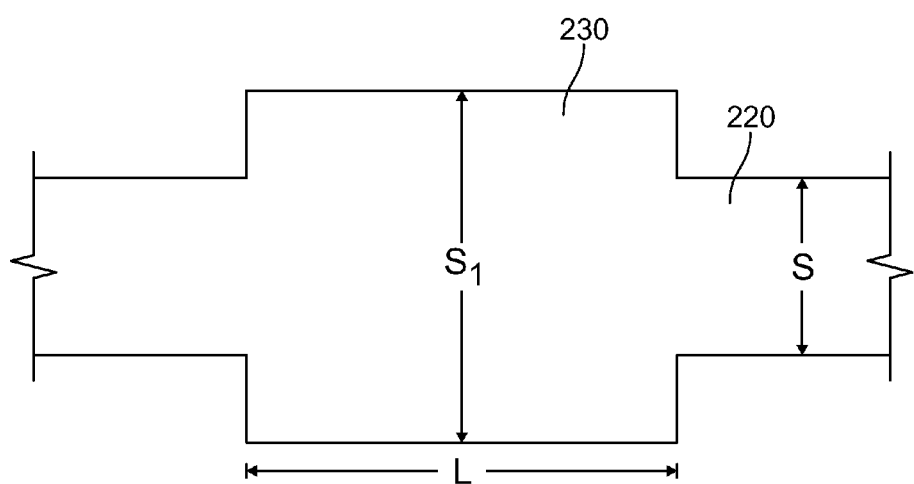
FIG. 2 illustrates the relationship between the area of an inlet port and an acoustic chamber for at least one embodiment of a PAP apparatus.

FIG. 2 illustrates a low-pass acoustic filter system. The equation below describe the effects modifying each geometrical section of the filter system has on the system.

$$T_\pi = \left( \frac{1}{1 + \left( \frac{S_1 - S}{2S} \right) kL} \right) \quad \text{Equation 1}$$

In Equation 1, T is the power transmission, also referred to as the acoustic output, sound level, or noise level; k is the wavenumber of the sound; S1 is the area of an acoustic chamber (e.g., chamber 230); L is the length of an acoustic chamber; and S is the area of an inlet port or tube (e.g., port 220). Thus, if S1 increases in size, L increases in length, or S decreases in area, then the power transmission T is reduced.

In accordance with the present disclosure, the area of the respective acoustic chamber (S1) and the area of its inlet port (S) may have a proportional relationship. For example, the area of the chamber may be larger than the area of the inlet port by a factor of 2. In additional embodiments, S1 may be larger than S by a factor ranging from a factor of approximately 2 to a factor of approximately 20 or more. In at least one embodiment, S1 is larger than S by a factor of about 10. Additionally, the length of L may be increased wherein the portion of the tube and the acoustic chamber effectively act as a single chamber, thus decreasing the amount of noise emanating from the system.

Referring to FIG. 2, the inlet pathway defined by S is smaller than the upstream portion of the acoustic chamber. In accordance with equation 1, when S is reduced relative to S1, then T or the noise level is attenuated. By increasing L (the length of the acoustic chamber), the noise may be further attenuated. In addition, if the inlet pathway is sufficiently long, the effective length of the acoustic chamber increases from L to L1, thus also reducing the noise of the system.

There exists a proportional relationship between the length of the inlet tube or port and the cross-sectional area of the inlet port with the volume (and length) of the receiving acoustic chamber. However increasing the length of the inlet port and restricting the cross-sectional area of the inlet port causes the resistance-to-air-flow in the system to increase. This may in turn cause a blower disposed inside an acoustic chamber to have to work harder, which may result in an increase in noise generated from the blower (or motor of the blower). Thus, a balancing and optimization step is often required when trying to create a sufficiently portable PAP device that is both quiet and small in size. Equation 2, illustrates this relationship of increasing or modifying the various dimensions of the inlet port and the effect it has on the increased motor work and noise.

$$\text{Resistance of air flow} \propto \frac{\text{Length inlet}}{\text{Area inlet}} \propto \text{Motor Work} \propto \text{Motor Noise} \quad \text{Equation 2}$$

Another way of describing this is a smaller inlet diameter increases air flow resistance, which increases motor noise. Some practical steps have been incorporated to also position inlet ports on the PAP device such that they point away from the ears of the user. For example, in several of the figures the inlet port is on the opposite end of the outlet port and adapters, which lead to the tubing that takes air to the mask placed over the user's nose and/or mouth. In several instances most of the noise escaping the system leaves through the inlet port.

Equation 1 can also be used to describe the relationship between length and noise attenuation in an individual tube. In the case of a single, individual tube, S1 is equal to S. Accordingly, the noise output T is reduced when the tube is lengthened (L is increased). This characteristic is important because the length of the intake tube (such as intake tube 115) can be used to decrease the noise of the PAP device (such as device 100 and other systems and methods described herein). Equation 3 describes the relationship between the cut-off frequency of the acoustic filtering and the length and areas of the chamber and tube:

$$f_c = \left( \frac{Sc}{\pi L (S_1 - S)} \right) \quad \text{Equation 3}$$

In equation 3: $f_c$ is the cutoff frequency; c is the speed of sound; S1 is the area of the expansion chamber; L is the length of the tube or chamber; and S is the area of inlet port. Thus, as L or S1 become larger in value, and/or S becomes smaller, the cutoff frequency becomes lower and every frequency above the cutoff frequency is significantly attenuated. In practical terms, the cutoff frequency $f_c$ can be reduced by increasing the ratio of S1:S, for example by decreasing the area of the inlet and/or increasing the area of the acoustic chamber. Additionally, lengthening the acoustic chamber (increase L) will also reduce the cutoff frequency.

Figure 3A:
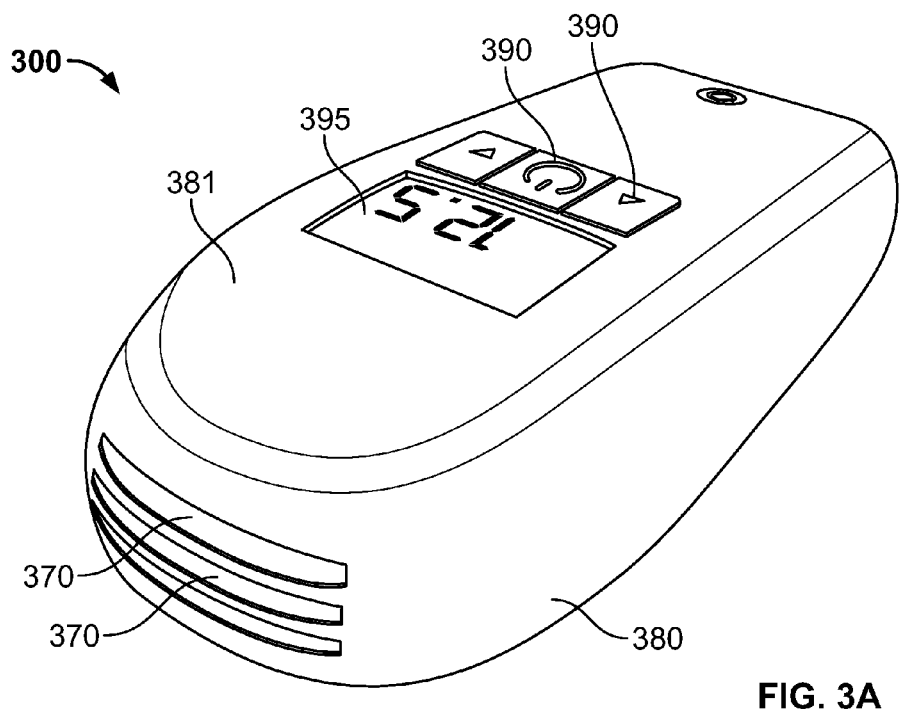
FIG. 3A depicts a perspective view of a portable PAP apparatus.

FIG. 3A depicts a perspective view of a portable PAP apparatus 300. Apparatus 300 includes a lower housing component 380 coupled with an upper housing component 381 to form an exterior enclosure for apparatus 300. Apparatus 300 includes a digital display 395 and user interface buttons 390 for controlling and using apparatus 300. For example, a user may be able to turn the power on and off, adjust pressure settings, set a timer, run system diagnostic tests, and control or adjust other functions. Display 395 may be any appropriate display, including, but not limited to an LED or LCD display. Although 1-3 user interface buttons 390 are depicted in FIG. 3A, any appropriate number of buttons may be used. In certain approaches, a PAP apparatus, such as apparatus 300, may include between 1 and 10 user interface buttons. In certain approaches, user interface buttons are included in display 395. For example, display 395 may be a capacitive or pressure-sensitive touch screen display. Further, display 395 may vary in size between different embodiments. For example, some embodiments may include a larger display, while other embodiments may include a smaller display. Display 395 may display data or control functions, such as pressure levels, time, use time, or other information. Display 395 may show one piece of data or function, or a plurality of data and functions.

Apparatus 300 includes intake vents 370. In certain approaches, intake vents 370 include a filtering system, such as filter 170 of device 100. The filtering system may comprise a lattice type structure capable of accepting a filter or filtering material. The filtering material may comprise any type of material commonly used to filter particles from the air.

PAP apparatus 300 may be any appropriate size. In certain approaches, apparatus has 300 has a length of between approximately 1 inches and approximately 10 inches, a width between approximately 1 inch and approximately 10 inches and a height between approximately 1 inch and approximately 10 inches. For example, in certain approaches, PAP apparatus 300 has dimensions of approximately 5.63 inches in height, 3.11 inches in width, and 1.75 in height. However, the length, width, and height may vary from embodiment to embodiment depending on the size of the blower or motor, the desired single chamber volume, or any other factor that may affect the external dimensions.

Figure 3B:
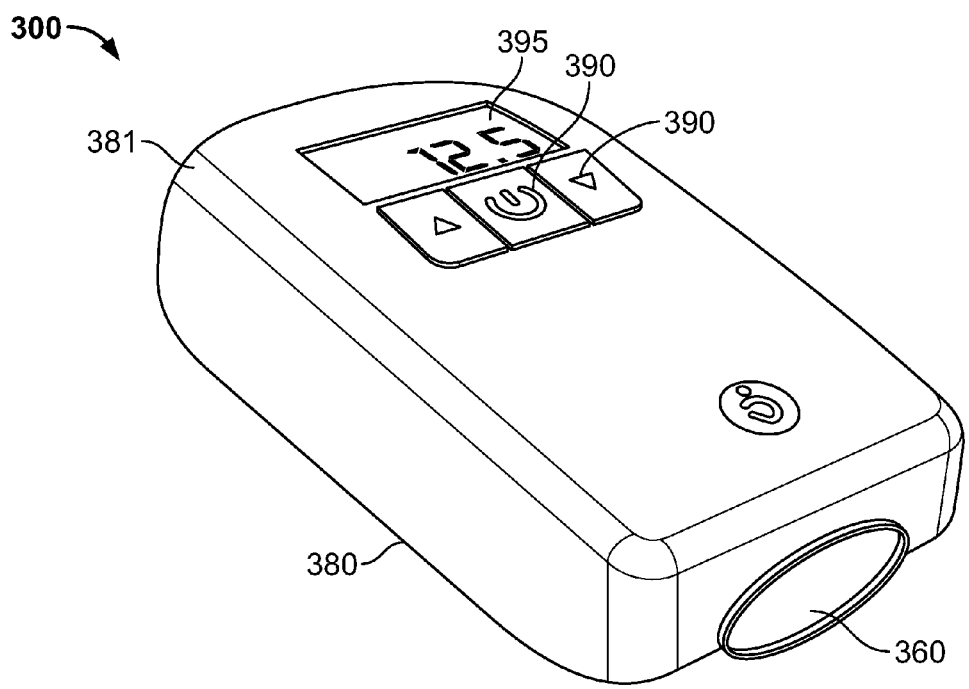
FIG. 3B illustrates a perspective view of a PAP apparatus, including an adapter portion.

FIG. 3B illustrates a perspective view of PAP apparatus 300, including an adapter 360. In certain approaches, adapter 360 is solitary in construction with the housing, such as lower housing component 380 and/or upper housing component 381. In certain embodiments, adapter 360 may be a separate piece, with a proximal portion secured within the interior portion of apparatus 300 and a distal portion extending outward from apparatus 300.

Figure 3C:
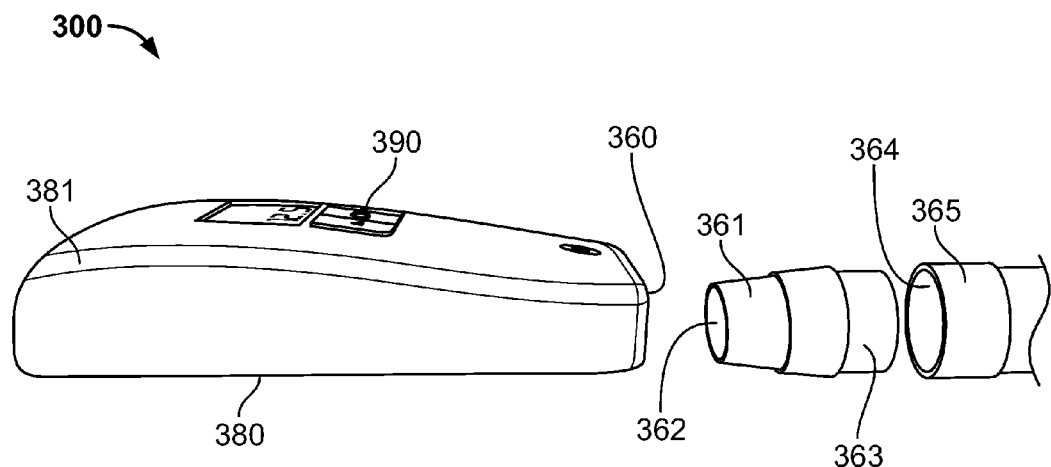
FIG. 3C illustrates a system for providing positive air pressure to a patient.

FIG. 3C depicts apparatus 300 with adapters and an interface components for providing positive air pressure to a patient. A male/female (m/f) adapter 361 couples to adapter 360 of apparatus 300. For example, first end 362 of adapter 361 may be a male end that couples within adapter 360. Male/female adapter 361 also couples to patient interface system 365. For example, second end 363 may be a male end that couples to proximal end 364 of patient interface system 365. In certain approaches, patient interface system 365 is shaped and configured to couple directly to apparatus 300, thus eliminating the need for an intermediate adapter, such as male/female adapter 361. In certain embodiments, the coupling ends, such as adapter 360, first end 362, second end 363, and proximal end 364 may have shapes such as ovals, to provide directional fit.

In certain embodiments, PAP apparatus 300 may include an outer casing. In some embodiments, the outer casing may further comprise an energy source. For example, the outer casing may include a battery or a power connector. In some embodiments, a battery pack or power source is directly attached or connected to the CPAP device.

Figure 4:
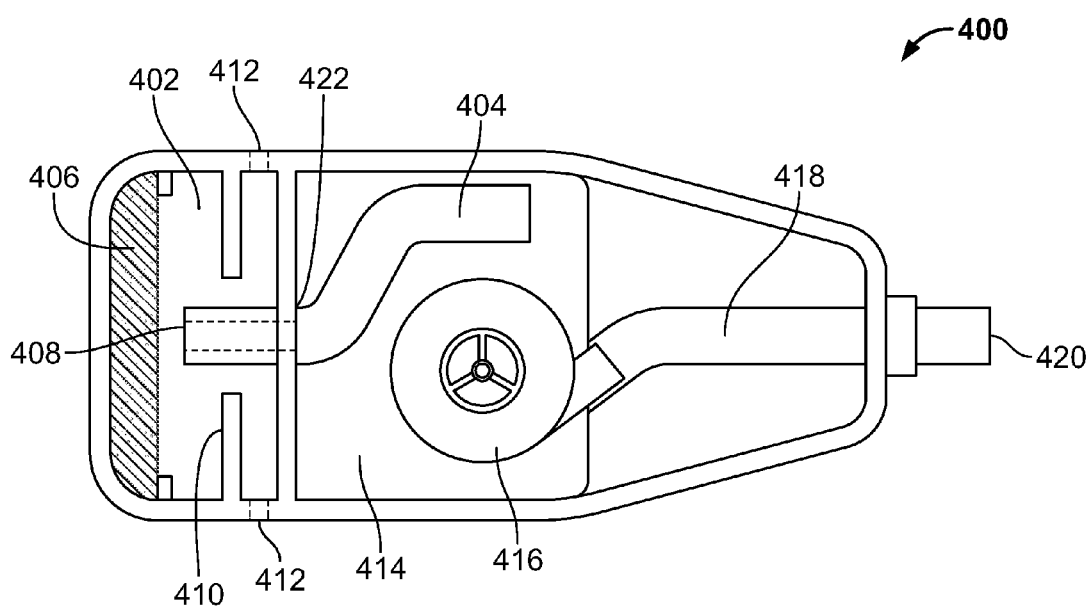
FIG. 4 depicts the interior of a portable PAP apparatus.

FIG. 4 depicts the interior of a portable PAP apparatus 400. PAP apparatus 400 includes an attenuation intake chamber 402 with sound attenuators 410 positioned within intake chamber 402. In certain approaches, intake chamber 402 includes foam 406 to reduce the acoustic output of apparatus 400. Although foam is described, any dissipative element could be used. Dissipative elements may include anechoic materials such as foam, rubber, clay, silicon, or any other suitable soft and/or porous materials. Additionally or alternatively, apparatus 400 includes intake vents 412, through which air may flow.

PAP apparatus 400 has an acoustic chamber 414 with an inlet port 422 coupled to intake chamber 402. An intake tube 404 extends from intake chamber 402, through inlet port 422, and into acoustic chamber 414. Intake tube 404 includes opening 408 to enable air flow from intake chamber 402 into acoustic chamber 414. When in operation, blower 416 is powered on and pulls air through vents 412 into opening 408, through tube 404, and into blower 416. Blower 416 then pushes air through outlet tube 418 and through opening 420 into a patient interface, such as patient interface 165.

The size and location of intake tube 404 and opening 408 may be determined based on the location and size of attenuators 410. Intake tube 404 may extend past attenuators 410. For example, opening 408 may have a diameter of approximately 0.5 inches and intake tube 404 may extend into attenuating intake chamber 402 approximately 0.875 inches beyond attenuators 410. In certain embodiments, the diameter of opening 408 along the length of intake tube 404 varies in diameter. For example, the diameter may vary from approximately 0.25 inches to 0.75 inches. In certain embodiments, intake tube 404 extends into attenuating intake chamber 402 so that opening 408 is substantially even with attenuators 410. In certain approaches, intake tube 414 extends past attenuators 410 by more than approximately 1 inch.

Figure 5:
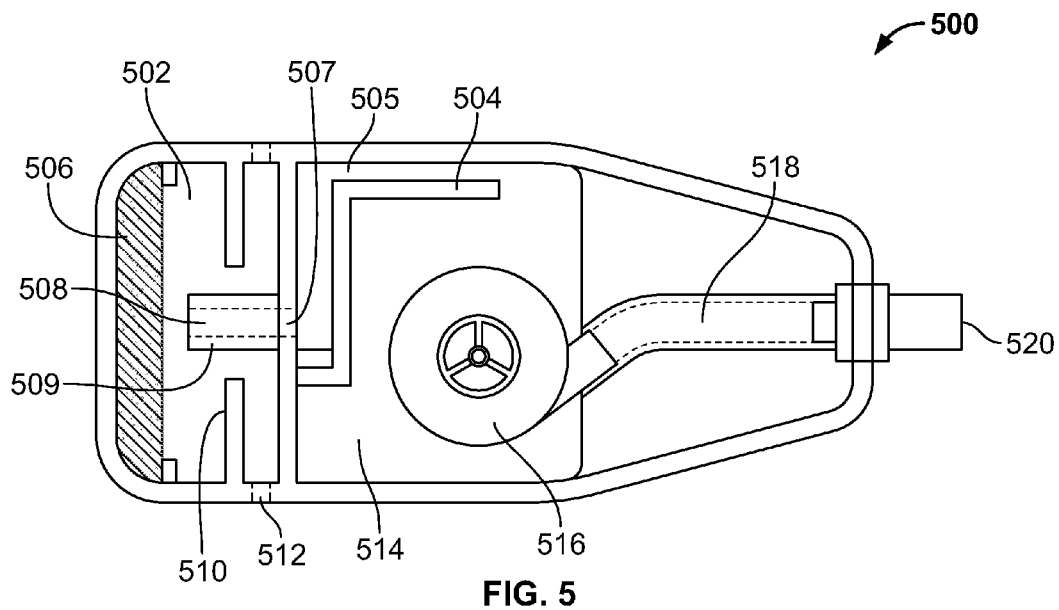
FIG. 5 is an illustrative example of a PAP apparatus.

FIG. 5 depicts the interior of a portable PAP apparatus 500. PAP apparatus 500 includes an attenuation intake chamber 502 with sound attenuators 510 positioned within intake chamber 502. In certain approaches, intake chamber 502 includes foam 506 to reduce the acoustic output of apparatus 500. Although foam is described, any dissipative element could be used. Dissipative elements may include anechoic materials such as foam, rubber, clay, silicon, or any other suitable soft and/or porous materials. Additionally or alternatively, apparatus 500 includes intake vents 512, through which air may flow.

PAP apparatus 500 has an acoustic chamber 514 coupled to intake chamber 502 via inlet port 507. In certain approaches, apparatus 500 includes a first intake tube 509 extending into intake chamber 502. Apparatus 500 includes a barrier 504, which forms a flow space 505, which is in fluid communication with first intake tube 509. As depicted, flow space 505 can have turns or bends. Barrier 504 may be configured such that flow space 505 defines any number of turns, wherein each turn has any angular dimension (e.g., sixty degrees, ninety-degrees, one-hundred-eighty degrees, etc.) and any combination of vertical and horizontal turns. In certain approaches, barrier 504 is firm and inflexible. When in operation, blower 516 is powered on and pulls air through vents 512, into opening 508 of intake tube 509, through tube 509, through inlet port 507, through flow space 505, into acoustic chamber 514, and into blower 516. Blower 516 then pushes air through outlet tube 518 and through opening 520 into a patient interface, such as patient interface 165.

Figure 6:
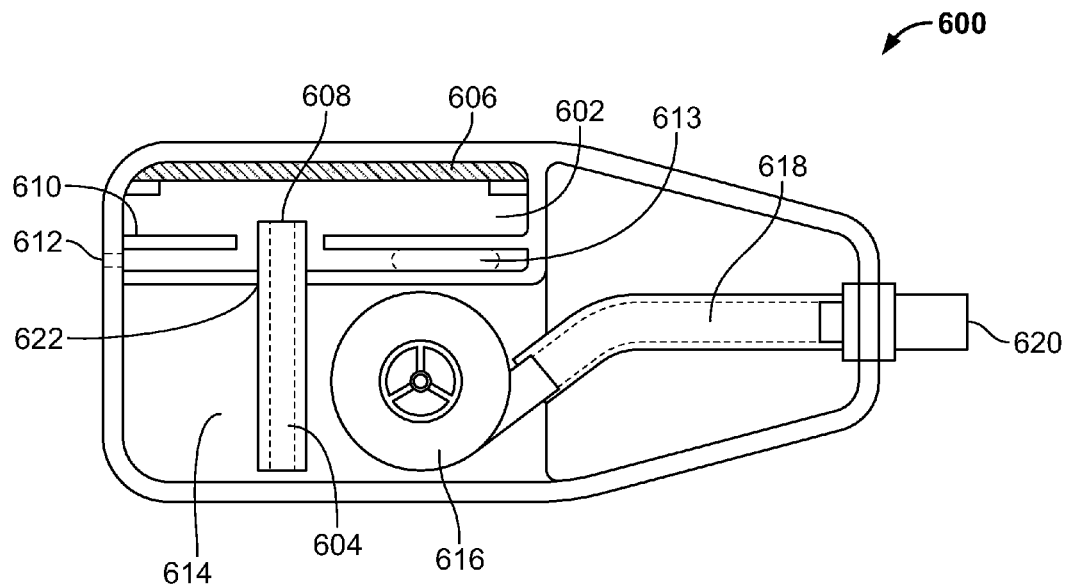
FIG. 6 illustrates the interior of a portable PAP apparatus.

The intake chamber may be on any appropriate side (e.g., back, side, top, bottom, etc.) of the apparatus. For example, FIG. 6 depicts the interior of a portable PAP apparatus 600 with an intake chamber 602 positioned on a side of apparatus 600. Intake chamber 602 includes sound attenuators 610 positioned within intake chamber 602. In certain approaches, intake chamber 602 includes foam 606 to reduce acoustic output of apparatus 600. Although foam is described, any dissipative element could be used. Dissipative elements may include anechoic materials such as foam, rubber, clay, silicon, or any other suitable soft and/or porous materials. Additionally or alternatively, apparatus 600 includes intake vents 612 and 613, through which air may flow. In the depicted example, intake vents 613 are positioned at the top and/or bottom of apparatus 600.

PAP apparatus 600 has an acoustic chamber 614 with an inlet port 622 coupled to intake chamber 602. An intake tube 604 extends from intake chamber 602, through inlet port 622, and into acoustic chamber 614. Intake tube 604 includes opening 608 to enable air flow from intake chamber 602 into acoustic chamber 614. Although depicted as straight, intake tube 604 may include any number of turns. When in operation, blower 616 is powered on and pulls air through vents 612 and vents 613, into opening 608, through tube 604, and into blower 616. Blower 616 then pushes air through outlet tube 618 and through opening 620 into a patient interface, such as patient interface 165.

FIGS. 7A-7D depict a PAP apparatus having an internal pressure sensor. CPAP device 700 is similar to previously described CAP devices and apparatuses, such as device 100. Device 700 has a lower housing component 780, which together with an upper housing component 784, defines sealed chamber 730. Sealed chamber 730 has an inlet port 710 and an outlet port 739. A motor or blower 740 is placed within chamber 730. In some embodiments, foam or another anechoic material (not depicted) may be placed within chamber 730 to further attenuate noise produced during the operation of device 700.

Device 700 additionally includes connector portion 785 to couple lower housing 780 and upper housing 784 together, thereby creating a seal. In the depicted example, connector portions 785 are positioned around the perimeter of the housing. A fastener, such as a screw, may be used to couple lower housing 780 and upper housing 784. Additionally or alternatively, the edge 782 of the housing may provide a coupling and/or sealing mechanism. For example, edge 782 may has a tongue, which fits into a groove on the edge of upper housing 784. Edge 782 may also include a seal, such as santoprene or silicone.

Inlet port 710 includes an intake tube 715 having a first end 712 extending through lower housing 780 and a second end 720 that extends into chamber 730. Intake tube 715 may have either a constant or varying internal diameter. The cross-sectional shape may be circular, square, oval, rectangular, triangular or any other shape. For example, the internal diameter may range from approximately 0.25 inches to approximately 0.75 inches and may have a length ranging from approximately 0.25 inches to approximately 3 inches, although any appropriate diameter and length may be used. The length and diameter of intake tube 715 affect the overall noise attenuation of the CPAP device, as previously discussed. Accordingly, in some approaches, the dimensions of intake tube 715 are proportionally related to the volume of chamber 730.

Intake tube 715 may be formed using rigid materials, flexible materials, or any combination thereof. For example, intake tube 715 may be formed using a hard plastic. In certain embodiments, intake tube 715 is composed of flexible polyvinylchloride (PVC) tubing, silicone tubing, or any other type of tubing commonly used in the art.

In certain approaches, outlet port 739 includes outlet tube 745, which extends from blower outlet 737 through the lower housing 780. An adapter 760 may be used to connect the blower outlet tube 745 to a patient interface, such as patient interface 165. Outlet tube 745 may also vary in length and diameter.

Apparatus 700 includes a pressure port 762. Pressure port 762 has a first end 764 on the exterior of lower housing 780 and upper housing 784. First end 764 is coupled to adapter 760. Pressure port 762 runs through housing 780 into chamber 730, where the second end 768 couples to pressure sensor 745. Pressure port 762 provides fluid communication from the output of device 700 at adapter 760 to pressure sensor 745. In certain approaches, sensor 745 is on circuitry board 744. Circuitry board 744 includes control circuitry and control components for the operation of device 700. Circuitry board 744 may be positioned over outlet tube 745. In certain approaches, circuitry board 744 includes a power source, such as a power adapter or battery. In certain approaches, the control circuitry on board 744 of device 700 is configured to display the pressure measured by pressure sensor 745 through pressure port 762 at display 788 of control panel 786 on upper housing 784. Display 788 may be similar to previously described display 395. In certain embodiments, the pressure output of device 700 may be adjusted manually by the user with user interface buttons 785. User interface buttons 785 may be similar to previously described buttons 390. In certain approaches, the control circuitry on board 744 is configured to automatically adjust the output of device 700 based on the pressure measurements from pressure sensor 745. The output of device 700 may be adjusted by modulating the power of blower 740.

During operation, PAP device 700 creates positive air pressure through outlet port 739. For example, when a patient interface is attached to adapter 760, PAP device 700 creates positive air pressure, which can be provided to the patient when the patient places the adapter at his or her airways (e.g., nose or mouth). When blower 740 is powered on, blower 740 pulls air through inlet port 710 into chamber 730 and into blower 740. Blower 740 then pushes air through outlet 737, through outlet tube 745, and through outlet port 739 to thereby provide positive air pressure through outlet port 739.

Figure 7A:
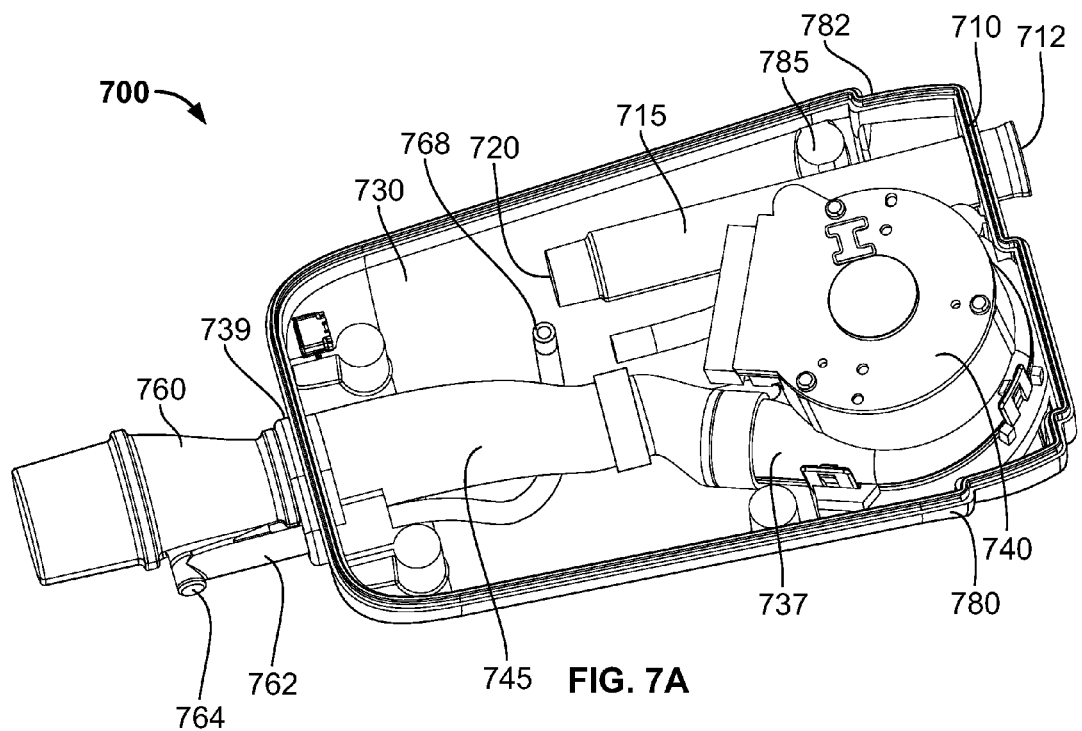
FIGS. 7A-7D depict a PAP apparatus having an internal pressure sensor.
Figure 7B:
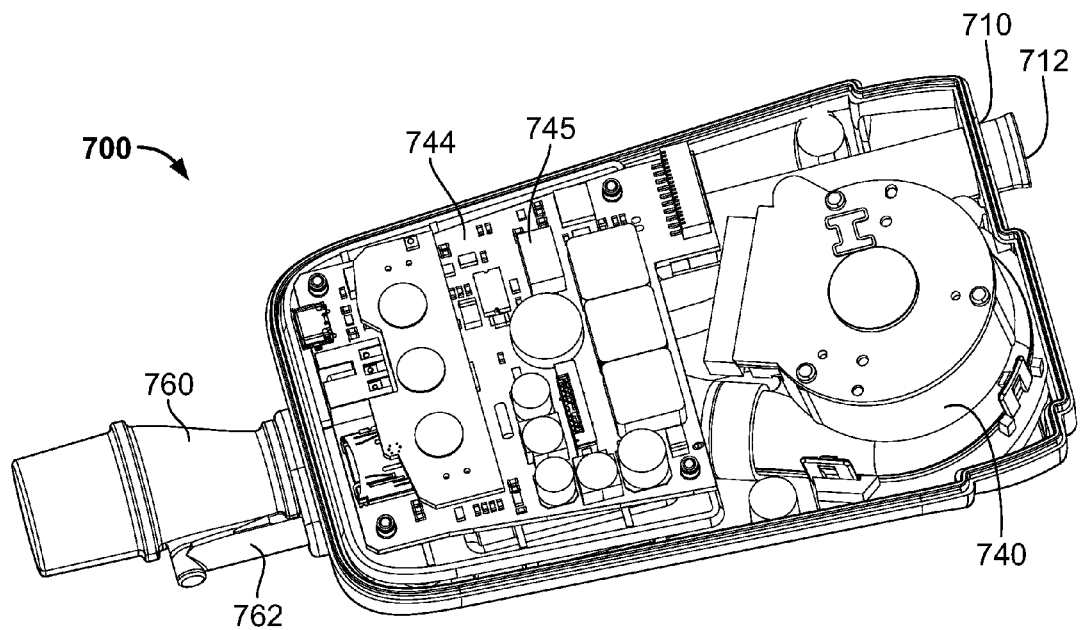
Figure 7C:
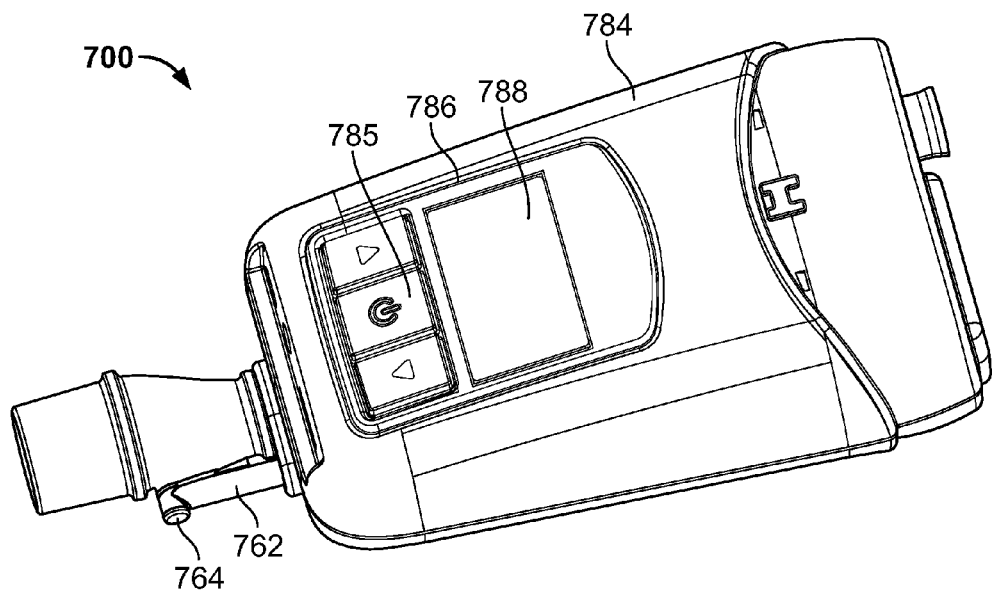
Figure 7D:
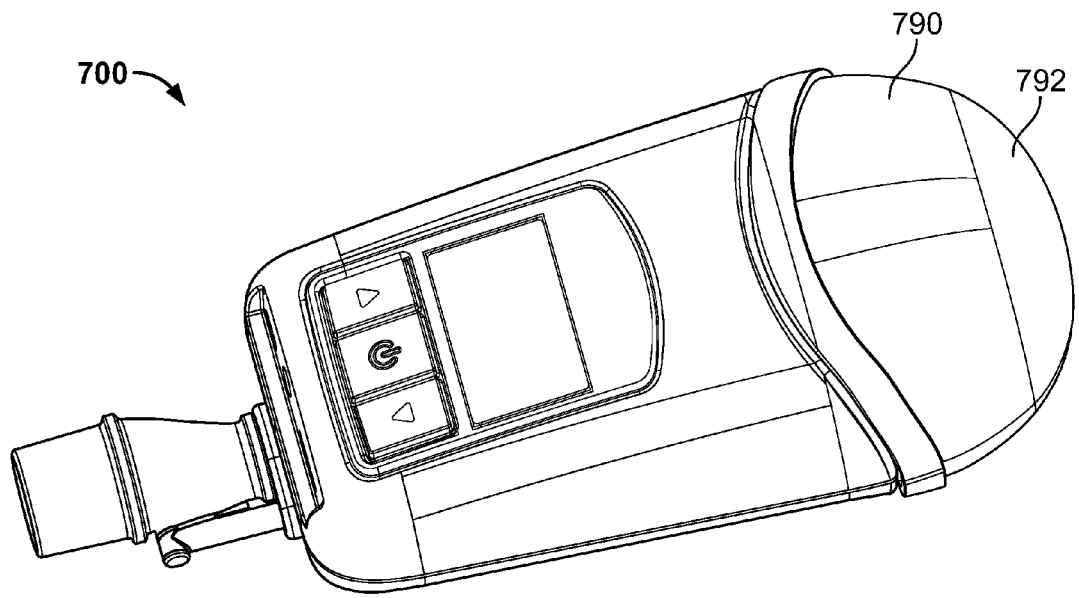

As depicted in FIG. 7D, device 700 may include an intake cover 790. Intake cover 790 serves to prevent the occlusion of inlet port 710 during use of device 700. Intake cover 790 includes a vented portion 792 to allow the pass through of air during operation of device 700. In certain embodiments, intake cover 790 may include a filter to clean the air of particulate matter. In certain embodiments, intake cover 790 is removable so that it may be cleaned, replaced, or adapted for a particular need.

In certain embodiments, air may be passed through intake cover 790 before entering inlet port 710. In certain approaches, the pressurized air is delivered to a patient through a patient interface at a pressure ranging from approximately 2 centimeters (cm) of water to approximately 40 cm of water above atmospheric pressure at the point of use, although any appropriate pressure may be used.

Figure 8A:
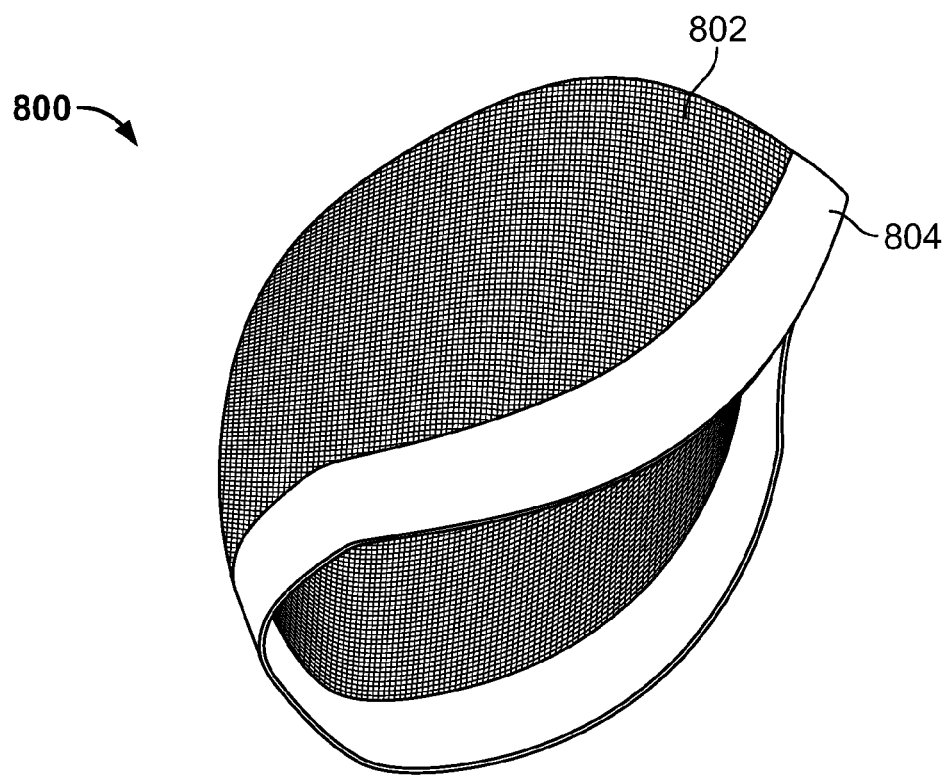
FIGS. 8A-B illustrate a cover for a PAP apparatus.

FIG. 8A depicts one embodiment of an acoustically invisible cover 800. Cover 800 may be similar to cover 790 and is positioned on the housing over the inlet port (such as inlet port 110 or inlet port 710) to prevent occlusion of the inlet port during use. Cover 800 includes a first portion 804, which is shaped similar to the housing of a PAP device (such as device 100 or device 700) so that it can couple directly to the housing. Cover 800 includes a flow portion 802, which is sufficiently porous so that air can flow through it. In certain embodiments, flow portion 802 is constructed of a mesh material, such as a metal or plastic. For purposes of this application 'acoustically invisible' is defined as not adding more than 3 dBA of sound to the overall PAP device. Ideally less than 1 dBA, or less than 0.5 dBA or something even less negligible is achieved.

Figure 8B:
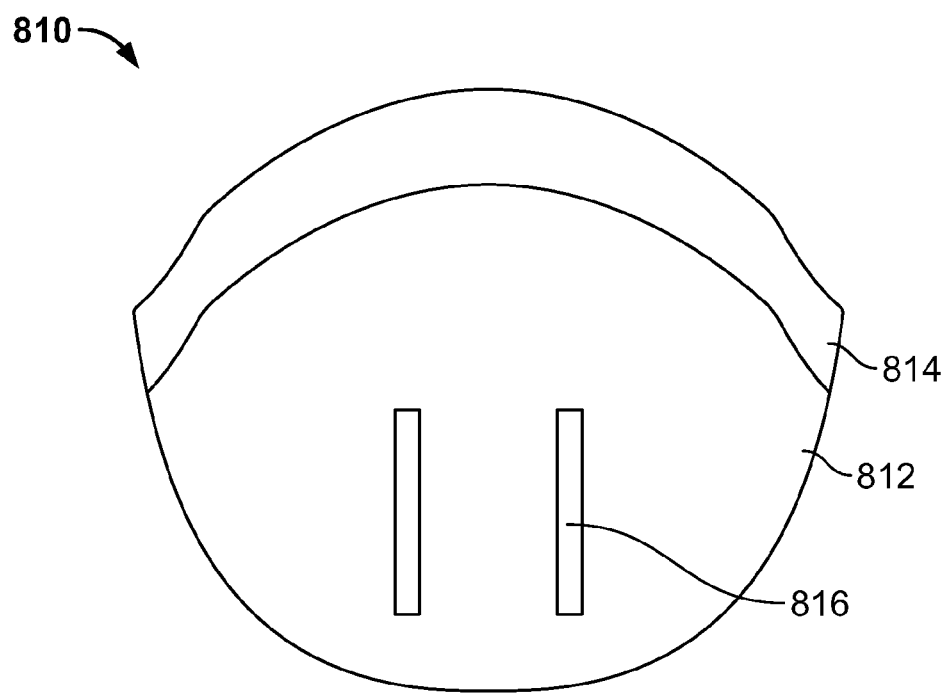

FIG. 8B depicts an embodiment of a cover 810. Cover 810 may be similar to cover 790 or cover 800 and is positioned on the housing over the inlet port (such as inlet port 110 or inlet port 710) to prevent occlusion of the inlet port during use. Cover 810 includes a first portion 814, which is shaped similar to the housing of a PAP device (such as device 100 or device 700) so that it can couple directly to the housing. Cover 810 includes flow portion 812, which is sufficiently porous so that air can flow through it. For example, flow portion 812 may be constructed of paper or mesh. In certain approaches, flow portion 812 includes vents such as vents 816. However, if flow portion 812 were not constructed of mesh, paper, or plastic that was sufficiently porous and was solid instead, the vents 816 may actually cause the overall dBA of the device to increase such that it would not be acoustically invisible.

In the absence of any additional outside attenuators, the CPAP device disclosed herein, having one interior attenuator, produces noise levels of about 30 dBA or less. In some instances as low as 26 dBA or less.

Figure 9:
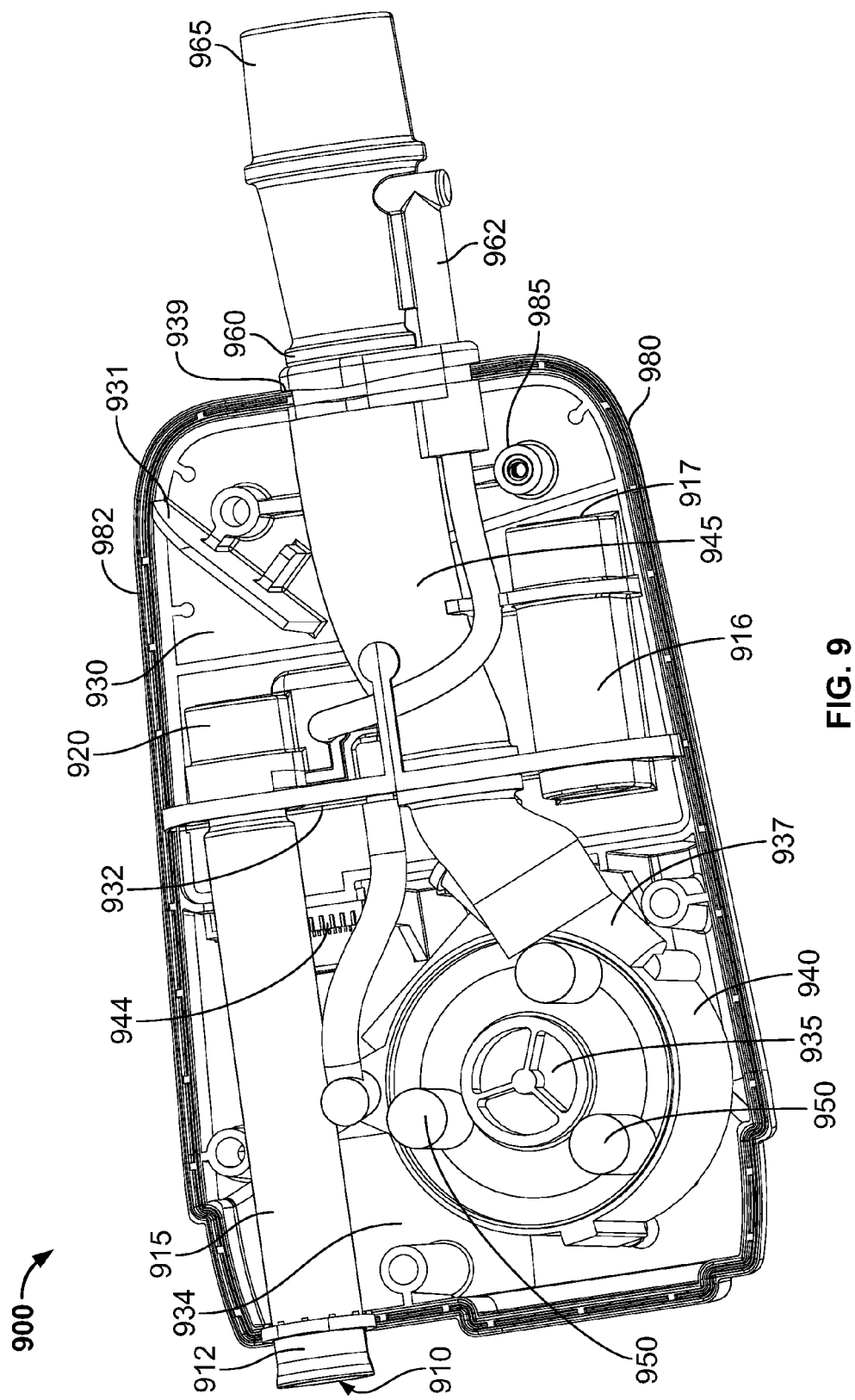
FIG. 9 is a perspective view of the interior of a multi-chamber PAP apparatus.

FIG. 9 depicts the interior of a dual chamber PAP apparatus 900. CPAP device 900 has a lower housing component 980, which together with an upper housing component (not shown) defines a first sealed chamber 930 and a second sealed chamber 934 separated by wall 932. First sealed chamber 930 has an inlet port 910 with intake tube 915, which extends through housing 980, through second chamber 934, and through wall 932 into first chamber 930. A first portion 912 of tube 915 is outside housing 980 and a second portion 920 is inside sealed chamber 930. In some embodiments, the first chamber may further include a noise attenuator 931 positioned within the airflow path from portion 920 of intake tube 915. Again for clarity, tubes described do not necessarily have to be circular in cross-section or round. They can include square, rectangular, and other shapes.

Device 900 includes an interchamber port 917, which allows air to flow from the first chamber 930 to the second chamber 934. In certain approaches, interchamber port 917 includes a tube 916, which extends from first chamber 930, through wall 932, and into second chamber 934.

The first and second chambers are separated by a chamber wall 932. In some embodiments, chamber wall 932 may be formed on lower housing 932 and/or the upper housing (not depicted). In certain approaches, chamber wall 932 is solitary in construction with the housing. Additionally or alternatively, chamber wall 932 may be secured to the respective housing components with an adhesive or glue. Additionally or alternatively, chamber wall 932 may be formed from an anechoic material such as foam, rubber, clay, silicon, or any other suitable soft and/or porous materials. In certain embodiments, chamber wall 932 may be formed using a rigid material, such as a hard plastic.

A motor or blower 940 is located within second chamber 934. In certain embodiments, blower 940 is secured to chamber 934 using one or more mount connects 950. In some embodiments, the mount connects may further comprise pivoting cone connectors, circular donut shaped mount connects, a silicone cradle, or any combination thereof. For example, the mount connects may comprise pivoting cone connectors that connect the top of blower 940 within chamber 934 and circular donut shaped mount connects that connect the bottom of blower 940 within chamber 930. In addition to connecting blower 940 to the housing, mount connects 940 may reduce or eliminate transfer of vibrations from the blower to other components of device 900. In certain embodiments, blower 940 is a brushless air-bearing motor.

In some embodiments, foam or another anechoic material may be placed within chamber 930 and chamber 934 to further attenuate noise produced during the operation of device 900. The anechoic or noise attenuating material may be secured at specific locations within each chamber. In additional embodiments, the lower and/or upper housing components may be lined with an anechoic or noise attenuating material. In such embodiments, the anechoic or noise attenuating material may include foam, rubber, clay, silicon, or any other suitable soft and/or porous materials.

In at least one embodiment, first chamber 930 further comprises an attenuator 931 which may be placed within the chamber directly across from the proximal end 920 of intake tube 915. Attenuator 931 is positioned within the airflow path to thereby attenuate noise created by the flow of air through chamber 930. In certain approaches, attenuator 931 is angled toward the intake tube having an acute angle relative to the housing component. In certain approaches, device 900 includes a plurality of attenuators. In certain approaches, device 900 includes at least one attenuator in second chamber 934. When a plurality of attenuators are included, each attenuator, such as attenuator 931, within the chamber 930 or chamber 934 may be oriented in varying angles relative to the end of intake tube 915, interchamber tube 916, and/or the housing components. While the attenuators may vary in size, length, quantity, shape, angle, and/or location, they may divert the airflow pathway and reduce the amount of noise exiting the CPAP device. Attenuators may further comprise a dissipative element, noise attenuating coating, and/or a noise attenuating material attached thereto. For example, attenuator 931 may be composed of or coated with an anechoic or noise attenuating material. The anechoic or noise attenuating material may include foam, rubber, clay, silicon, or any other suitable soft and/or porous materials.

Device 900 additionally includes one or more connector portions 985 to couple lower housing 980 and upper housing together, thereby creating a seal. In the depicted example, the connector portions 985 are positioned around the perimeter of the housing. A fastener, such as a screw, may be used to couple the housing. Additionally or alternatively, edge 982 of the housing may provide a coupling and/or sealing mechanism. For example, edge 982 has a tongue, which may couple to a groove in an upper housing portion. Edge 982 may also include a seal, such as santoprene or silicone.

Intake tube 915 and interchamber tube 916 may have either a constant or varying internal diameter. For example, an interior diameter may range from approximately 0.25 inches to approximately 0.75 inches and may have a length ranging from approximately 0.25 inches to approximately 3 inches, although any appropriate diameter and length may be used. The length and diameter of intake tube 915 affect the overall noise attenuation of the CPAP device, as further discussed in relation to FIG. 2 and equation 1 and equation 2. Accordingly, in some approaches, the dimensions of intake tube 915 and interchamber tube 916 are proportionally related to the volume of chamber 930.

Intake tube 915 and interchamber tube 916 may be formed using rigid materials, flexible materials, or any combination thereof. For example, intake tube 915 and interchamber tube 916 may be formed using a hard plastic. In certain embodiments, intake tube 915 and interchamber tube 916 are composed of flexible polyvinylchloride (PVC) tubing, silicone tubing, or any other type of tubing commonly used in the art. Intake tube 915 and interchamber tube 916 may be composed of different materials.

In certain approaches, outlet port 939 includes outlet tube 945, which extends from blower outlet 937 into second chamber 934, through wall 932, through first chamber 930, and through housing 980. An adapter 960 may be used to connect the blower outlet tube 945 to patient interface 965. In embodiments having an adapter, the adapter may be solitary in construction and configured so that a proximal portion of the adapter may be secured and sealed to the housing of device 900, while a distal portion of the adapter extends outward from device 900. The lower housing component 980 and the upper housing component may each include a detent (not pictured) capable of accepting a portion of the adapter, whereby the two housing components together form a seal around the circumference of a portion of the adapter.

Outlet tube 945 may also vary in length and diameter. The length of the blower outlet tube 945 is long enough to connect to outlet 937 of blower 940 through outlet port 939. Outlet tube 945 provides a sealed airway between blower 940 and adapter 960 and/or patient interface system 965. Additionally, depending on the dimensions of blower 940, the inner diameter of the outlet tube 945 may vary so long as the diameter is large enough to fit over and seal with outlet 937 and adapter 960 and/or patient interface system 965. Outlet tube 945 may be formed using rigid materials, flexible materials, or any combination thereof. For example, outlet tube 945 may be formed using a hard plastic. In certain embodiments, outlet tube 945 is composed of flexible polyvinylchloride (PVC) tubing, silicone tubing, or any other type of tubing commonly used in the art.

Apparatus 900 includes a pressure port 962. Pressure port 962 is coupled to adapter 960. Pressure port 962 runs through housing 980 into chamber 930, where pressure port 962 couples to a pressure sensor, such as a pressure sensor on circuitry board 944. Pressure port 962 provides fluid communication from the output of device 900 at adapter 960 to a pressure sensor coupled to control circuitry. Circuitry board 944 includes control circuitry and control components for the operation of device 900. Circuitry board 944 may be positioned over or under outlet tube 945. In certain approaches, circuitry board 944 includes a power sources, such as a power adapter or battery. In certain approaches, the control circuitry on board 944 of device 900 is configured to display the pressure measured through pressure port 962 at a display, such as display 788 depicted in FIG. 7. In certain embodiments, the pressure output of device 900 may be adjusted manually by the user with user interface buttons. In certain approaches, the control circuitry on board 944 is configured to automatically adjust the output of device 900 based on the pressure measurements. The output of device 900 may be adjusted by modulating the power of blower 940.

Although not depicted, device 900 may include a cover, such as cover 790, cover 800, or cover 810, which covers and prevents the occlusion of inlet port 910

During operation, PAP device 900 creates positive air pressure through outlet port 939. For example, when patient interface 965 is attached, PAP device 900 creates positive air pressure, which can be provided to the patient when the patient places the adapter at his or her airways (e.g., nose or mouth). Blower 940 includes intake 935. When blower 940 is powered on, blower 940 intakes air through intake 935 and pushes out that air through outlet 937. The reduced pressure at intake 935 causes air to flow through inlet port 910 into chamber 930, where it then flows through interchamber port 917 into second chamber 934, and into intake 935 of blower 940. Blower 940 then pushes the air through outlet 937, through outlet tube 945, and through outlet port 939 to thereby provide positive air pressure through outlet port 939. In certain embodiments, air may be initially passed through a pre-intake chamber, such as pre-intake chamber 172 as described in relation with device 100, before entering inlet port 910. In certain approaches, the pressurized air is delivered to a patient through patient interface 965 at a pressure ranging from approximately 2 centimeters (cm) of water to approximately 40 cm of water above atmospheric pressure at the point of use, although any appropriate pressure may be used.

Both the first chamber 930 and second chambers 934 may be designed to reduce the amount of noise released from CPAP device 900 during operation. In such embodiments, the chambers may be designed to operate as a high-pass, low-pass, band filter, or a combination thereof. For example, in one embodiment, first chamber 930 may be designed as a low-pass filter, while second chamber 934 is designed as a high-pass filter. In additional embodiments, first chamber 930 and second chamber 934 may both operate as low-pass filters.

In certain approaches, first chamber 930 and second chamber 934 have a combined volume ranging from approximately 200 milliliters (mL) to approximately 485 mL. For example, the combined volume of first chamber 930 and second chamber 934 may be approximately 481 mL. The combined volume of first chamber 930 and second chamber 934 may be approximately 395 mL. The combined volume of first chamber 930 and second chamber 934 may be less than 360 mL.

Additionally or alternatively, first chamber 930 and second chamber 934 may have equivalent volumes. In certain approaches, one of the chambers may have a larger volume than the other chamber. In certain embodiments the second acoustic chamber, which houses the blower, is larger than the first acoustic chamber. For example, in an embodiment where the combined volume is approximately 270 mL, first chamber 930 may have a volume ranging from approximately 70 mL to approximately 170 mL, and second chamber 934 may have a volume ranging from approximately 100 mL to approximately 200 mL. As an additional example, in an embodiment where the combined volume is approximately 480 mL, first chamber 930 may have a volume ranging from approximately 100 mL to approximately 240 mL, while second chamber 934 may have a volume ranging from approximately 240 mL to approximately 380 mL.

In some embodiments it is advantageous to have the first acoustic chamber (such as 930) proportionally sized to the inlet port 910, yet be smaller than the second acoustic chamber 934, such that a sufficiently sized blower and its motor may be completely disposed within the second acoustic chamber.

As is shown in both Equation 1 and FIG. 2, inlet port 910 and interchamber port 917 may each have a cross-sectional area that is proportionally related to the volume of chambers 930 and 934 respectively and balanced with the necessary work of the motor required to generate a desired amount flow. As previously mentioned, this increase in work may increase the noise generated by the blower and thus needs to be balanced with the cross-sectional areas of the ports 910 and 917. In other embodiments however, inlet ports may be designed without using Equations 1 & 2.

The above description is merely illustrative. Having thus described several aspects of at least one embodiment of this invention including the preferred embodiments, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawing are by way of example only.

What is claimed is:

1. A portable Continuous Positive Airway Pressure (CPAP) apparatus, comprising:
    a housing, wherein the housing defines a first acoustic chamber and a second acoustic chamber, the first acoustic chamber having a volume and a first inlet port, the first inlet port defining a length and cross-sectional area that is proportionally related to the volume of the first chamber, the second acoustic chamber having a volume and a second inlet port, wherein the second inlet port extends from the first acoustic chamber into the second acoustic chamber;
    a blower unit that being disposed within the second acoustic chamber; and
    wherein the first inlet port includes an intake tube which extends from an exterior portion of the second acoustic chamber, passes through an interior portion of the second acoustic chamber, and into the first acoustic chamber.

2. The apparatus of claim 1, wherein the length and cross-sectional area of the first inlet port and the volume of the first acoustic chamber are proportionally related so as to create a low-pass acoustic filter.

3. The apparatus of claim 1, wherein the combined volume of the first and second acoustic chambers is less than 360 milliliters.

4. The apparatus of claim 1, wherein the first inlet port further comprises a first intake tube having a diameter ranging from 0.25 inches to 0.75 inches and a length ranging from 0.25 inches to 3.5 inches.

5. The apparatus of claim 1, wherein the second inlet port further comprises a second intake tube having a diameter ranging from 0.25 inches to 0.75 inches and a length ranging from 0.25 inches to 3.5 inches.

6. The apparatus of claim 1, wherein the housing further comprises an anechoic material disposed therein.

7. The apparatus of claim 1, further comprising an adapter having a proximal end and a distal end, wherein the proximal end is in communication with the blower unit through a blower outlet tube and the distal end extending outward from the apparatus.

8. The apparatus of claim 7, wherein the blower outlet tube defines a sealed air-flow pathway between the blower unit and the adapter.

9. The apparatus of claim 1, wherein the housing further defines a hose port configured to receive a patient interface system.

10. The apparatus of claim 1, wherein the housing further comprises at least one user interface button.

11. The apparatus of claim 1, wherein the housing further comprises a digital display.

12. The apparatus of claim 1, wherein the housing further comprises an acoustically invisible cover positioned over the inlet port of the first acoustic chamber.

13. The apparatus of claim 1, wherein the first inlet port comprises an intake tube which passes through the second chamber into the first chamber and is sealed from the second chamber.

14. The apparatus of claim 13, further comprising an outlet tube extending from the blower in the second acoustic chamber and traversing through the first acoustic chamber and through the housing wall.

15. The apparatus of claim 1, wherein the cross-sectional area and length of the first inlet port is related to the noise generated by the blower, wherein the overall acoustic reduction is balanced with any increase in blower noise generated.

16. The apparatus of claim 1, wherein the volume of the second acoustic chamber is greater than the volume of the first acoustic chamber.

* * * * *